(12) United States Patent
Garde et al.

(10) Patent No.: US 8,986,375 B2
(45) Date of Patent: Mar. 24, 2015

(54) ANTI-PARAVALVULAR LEAKAGE COMPONENT FOR A TRANSCATHETER VALVE PROSTHESIS

(71) Applicant: Medtronic, Inc., Minneapolis, MN (US)

(72) Inventors: Kshitija Garde, Santa Ana, CA (US); Philip Haarstad, Minneapolis, MN (US); Igor Kovalsky, Minnetonka, MN (US); Stephen Nash, Ballybrit (IE); Gianfranco Pellegrini, Santa Rosa, CA (US); Finn Rinne, Santa Rosa, CA (US); Matthew Rust, Windsor, CA (US); Jeffrey Sandstrom, Forest Lake, MN (US); Padraig Savage, Ballybrit (IE); William Steinberg, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 12 days.

(21) Appl. No.: 13/795,066

(22) Filed: Mar. 12, 2013

(65) Prior Publication Data

US 2014/0277419 A1    Sep. 18, 2014

(51) Int. Cl.
*A61F 2/24*    (2006.01)

(52) U.S. Cl.
CPC ............ *A61F 2/2403* (2013.01); *A61F 2/2412* (2013.01); *A61F 2/2418* (2013.01)
USPC .......................... 623/2.18; 623/2.38; 623/1.26

(58) Field of Classification Search
USPC ............ 623/1.18, 1.31, 1.32, 2.17, 2.18, 2.38
See application file for complete search history.

(56) References Cited

U.S. PATENT DOCUMENTS

| | | | |
|---|---|---|---|
| 7,780,725 B2 | 8/2010 | Haug et al. | |
| 7,837,727 B2 | 11/2010 | Coetz et al. | |
| 8,052,741 B2 * | 11/2011 | Bruszewski et al. | 623/1.35 |
| 8,062,355 B2 * | 11/2011 | Figulla et al. | 623/2.1 |
| 2004/0111111 A1 | 6/2004 | Lin | |
| 2005/0203605 A1 | 9/2005 | Dolan | |
| 2007/0293944 A1 * | 12/2007 | Spenser et al. | 623/2.11 |

(Continued)

FOREIGN PATENT DOCUMENTS

EP           2537487        12/2012
WO    WO2011/057087         5/2011

OTHER PUBLICATIONS

U.S. Appl. No. 13/572,842, filed Aug. 13, 2012, Kovalsky.

(Continued)

*Primary Examiner* — Randy Shay

(57) ABSTRACT

A transcatheter valve prosthesis includes an expandable tubular stent, a prosthetic valve within the stent, and an anti-paravalvular leakage component coupled to and encircling the stent which includes a plurality of self-expanding struts and an annular sealing membrane. Each strut has a first end coupled to a distal end of the stent and a second end not coupled to the stent. Each anti-paravalvular leakage component is moveable between a compressed configuration and a deployed configuration. In the compressed configuration, each strut extends distally away from the distal end of the stent. In the deployed configuration, each strut extends proximally away from the distal end of the stent. In an embodiment hereof, the deployed strut has a C-shape and is twisted such that the C-shape lies in a plane substantially along or tangential with the outer surface of the stent. In another embodiment hereof, the deployed strut is rolled-up and extends radially away from the outer surface of the stent.

15 Claims, 12 Drawing Sheets

(56) References Cited

U.S. PATENT DOCUMENTS

| | | |
|---|---|---|
| 2008/0243245 A1 | 10/2008 | Thambar et al. |
| 2009/0099653 A1 | 4/2009 | Suri et al. |
| 2009/0276027 A1 | 11/2009 | Glynn |
| 2010/0168844 A1 | 7/2010 | Toomes et al. |
| 2010/0234940 A1 | 9/2010 | Dolan |
| 2011/0054466 A1 | 3/2011 | Rothstein et al. |
| 2011/0098802 A1 | 4/2011 | Braido et al. |
| 2011/0137397 A1* | 6/2011 | Chau et al. .................. 623/1.11 |
| 2011/0172765 A1 | 7/2011 | Nguyen et al. |
| 2011/0208283 A1 | 8/2011 | Rust |
| 2011/0264206 A1 | 10/2011 | Tabor |
| 2012/0035722 A1 | 2/2012 | Tuval |
| 2012/0101572 A1 | 4/2012 | Kovalsky et al. |

OTHER PUBLICATIONS

PCT/US2014/020872 Int'l Search Report and Written Opinion, May 19, 2014.

* cited by examiner

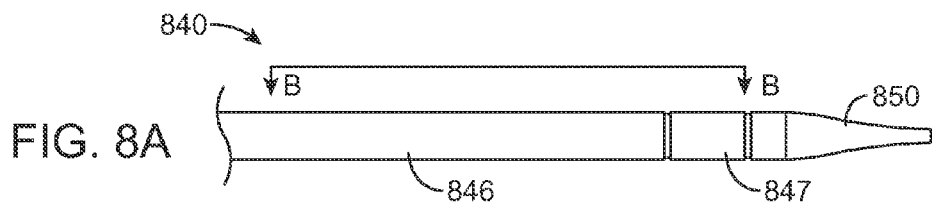
FIG. 8A
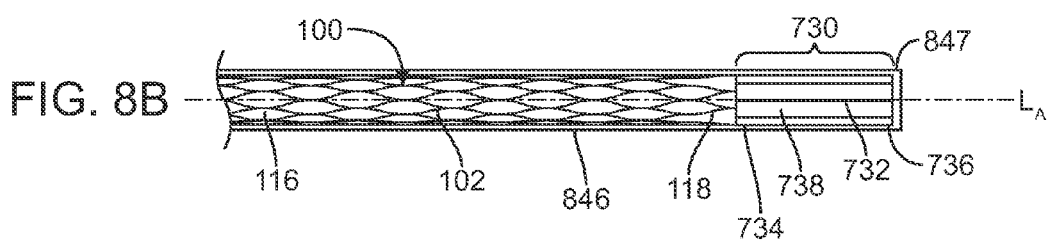
FIG. 8B
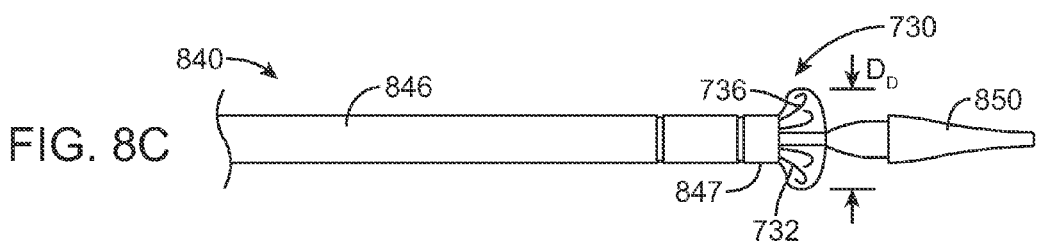
FIG. 8C
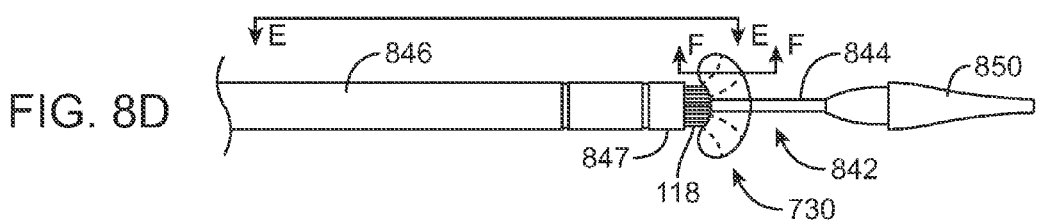
FIG. 8D
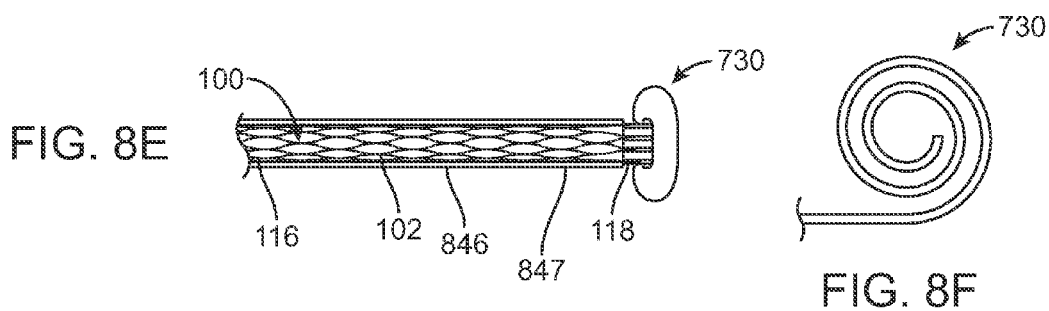
FIG. 8E
FIG. 8F

ANTI-PARAVALVULAR LEAKAGE COMPONENT FOR A TRANSCATHETER VALVE PROSTHESIS

FIELD OF THE INVENTION

The present invention relates to transcatheter valve prostheses and methods of preventing paravalvular leakage. More specifically, the present invention relates to an anti-paravalvular leakage component on a transcatheter valve prosthesis to seal gaps between a support frame of the prosthesis and native valve tissue.

BACKGROUND OF THE INVENTION

A human heart includes four heart valves that determine the pathway of blood flow through the heart: the mitral valve, the tricuspid valve, the aortic valve, and the pulmonary valve. The mitral and tricuspid valves are atrioventricular valves, which are between the atria and the ventricles, while the aortic and pulmonary valves are semilunar valves, which are in the arteries leaving the heart. Ideally, native leaflets of a heart valve move apart from each other when the valve is in an open position, and meet or "coapt" when the valve is in a closed position. Problems that may develop with valves include stenosis in which a valve does not open properly, and/or insufficiency or regurgitation in which a valve does not close properly. Stenosis and insufficiency may occur concomitantly in the same valve. The effects of valvular dysfunction vary, with regurgitation or backflow typically having relatively severe physiological consequences to the patient.

Recently, flexible prosthetic valves supported by stent structures that can be delivered percutaneously using a catheter-based delivery system have been developed for heart and venous valve replacement. These prosthetic valves may include either self-expanding or balloon-expandable stent structures with valve leaflets attached to the interior of the stent structure. The prosthetic valve can be reduced in diameter, by crimping onto a balloon catheter or by being contained within a sheath component of a delivery catheter, and advanced through the venous or arterial vasculature. Once the prosthetic valve is positioned at the treatment site, for instance within an incompetent native valve, the stent structure may be expanded to hold the prosthetic valve firmly in place. One example of a stented prosthetic valve is disclosed in U.S. Pat. No. 5,957,949 to Leonhardt et al. entitled "Percutaneous Placement Valve Stent", which is incorporated by reference herein in its entirety. Another example of a stented prosthetic valve for a percutaneous pulmonary valve replacement procedure is described in U.S. Patent Application Publication No. 2003/0199971 A1 and U.S. Patent Application Publication No. 2003/0199963 A1, both filed by Tower et al., each of which is incorporated by reference herein in its entirety.

Although transcatheter delivery methods have provided safer and less invasive methods for replacing a defective native heart valve, leakage between the implanted prosthetic valve and the surrounding native tissue is a recurring problem. Leakage sometimes occurs due to the fact that minimally invasive and percutaneous replacement of cardiac valves typically does not involve actual physical removal of the diseased or injured heart valve. Rather, the replacement stented prosthetic valve is delivered in a compressed condition to the valve site, where it is expanded to its operational state within the native valve. Calcified or diseased native leaflets are pressed to the side walls of the native valve by the radial force of the stent frame of the prosthetic valve. These calcified leaflets do not allow complete conformance of the stent frame with the native valve and can be a source of paravalvular leakage (PVL). Significant pressure gradients across the valve cause blood to leak through the gaps between the implanted prosthetic valve and the calcified anatomy.

Embodiments hereof are related to anti-paravalvular leakage components coupled to an outer surface of the valve prosthesis to seal gaps between the valve prosthesis and native valve tissue.

BRIEF SUMMARY OF THE INVENTION

Embodiments hereof relate to a transcatheter valve prosthesis including a tubular stent having a compressed configuration for delivery within a vasculature and an expanded configuration for deployment within a native heart valve, a prosthetic valve component disposed within and secured to the stent, and a plurality of self-expanding struts. Each strut has a first end coupled to a distal end of the tubular stent and a second end not coupled to the tubular stent. Each strut is moveable between a compressed configuration and a deployed configuration. In the compressed configuration, each strut extends distally away from the distal end of the stent. In the deployed configuration, each strut has a C-shape that extends proximally away from the distal end of the stent and is twisted such that the C-shape is oriented substantially flush with the outer surface of the stent.

Embodiments hereof also relate to a transcatheter valve prosthesis including a tubular stent having a compressed configuration for delivery within a vasculature and an expanded configuration for deployment within a native heart valve, a prosthetic valve component disposed within and secured to the stent, and an anti-paravalvular leakage component coupled to and encircling an outer surface of the tubular stent. The anti-paravalvular leakage component includes a plurality of self-expanding struts and an annular sealing membrane coupled to the struts. Each strut has a first end coupled to a distal end of the tubular stent and a second end not coupled to the tubular stent. Each anti-paravalvular leakage component is moveable between a compressed configuration and a deployed configuration. In the compressed configuration, each strut extends distally away from the distal end of the stent. In the deployed configuration, each strut has a C-shape that extends proximally away from the distal end of the stent and is twisted such that the C-shape is oriented substantially flush with the outer surface of the stent.

Embodiments hereof also relate to a transcatheter valve prosthesis including a tubular stent having a compressed configuration for delivery within a vasculature and an expanded configuration for deployment within a native heart valve, a prosthetic valve component disposed within and secured to the stent, and an anti-paravalvular leakage component coupled to and encircling an outer surface of the tubular stent. The anti-paravalvular leakage component includes a plurality of self-expanding struts and an annular sealing membrane coupled to the struts. Each strut has a first end coupled to a distal end of the tubular stent and a second end not coupled to the tubular stent. Each anti-paravalvular leakage component is moveable between a compressed configuration and a deployed configuration. In the compressed configuration, each strut extends distally away from the distal end of the stent. In the deployed configuration, each strut is rolled-up and extends radially away from the distal end of the stent.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 8A illustrates a side view of the heart valve prosthesis of FIG. 7 in a delivery or compressed configuration, loaded into a delivery system, according to an embodiment hereof.

FIG. 8B is a sectional view taken along line B-B of FIG. 8A.

FIGS. 8C-8D illustrate side views of the valve prosthesis of FIG. 8A, wherein a sheath of the delivery system is progressively retracted to expose and release the anti-paravalvular leakage component.

FIG. 8E is a sectional view taken along line E-E of FIG. 8D.

FIG. 8F is a cross-sectional view taken along line F-F of FIG. 8D.

DETAILED DESCRIPTION OF THE INVENTION

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician. In addition, as used herein, the terms "outward" or "outwardly" refer to a position radially away from a longitudinal axis of the stent and the terms "backward" or "backwardly" refer to the relative transition from a proximal position to a distal position. The following detailed description is merely exemplary in nature and is not intended to limit the invention or the application and uses of the invention. Although the description of the invention is in the context of treatment of heart valves, the invention may also be used where it is deemed useful in other valved intraluminal sites that are not in the heart. For example, the present invention may be applied to venous valves as well. Furthermore, there is no intention to be bound by any expressed or implied theory presented in the preceding technical field, background, brief summary or the following detailed description.

Figure 1:
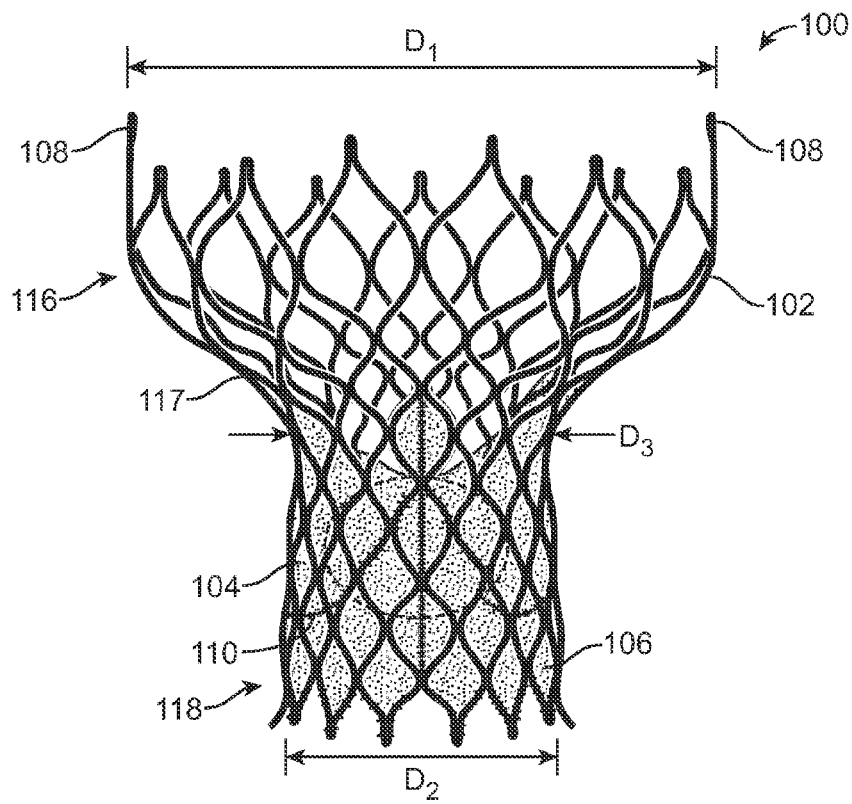
FIG. 1 is a side view illustration of an exemplary transcatheter heart valve prosthesis for use in embodiments hereof.

FIG. 1 depicts an exemplary transcatheter heart valve prosthesis 100. Heart valve prosthesis 100 is illustrated herein in order to facilitate description of the methods and devices to prevent and/or repair paravalvular leakage according to embodiments hereof. It is understood that any number of alternate heart valve prostheses can be used with the methods and devices described herein. Heart valve prosthesis 100 is merely exemplary and is described in more detail in U.S. Patent Application Pub. No. 2011/0172765 to Nguyen et al., which is herein incorporated by reference in its entirety.

Heart valve prosthesis 100 includes an expandable stent or frame 102 that supports a prosthetic valve component within the interior of stent 102. In embodiments hereof, stent 102 is self-expanding to return to an expanded deployed state from a compressed or constricted delivery state and may be made from stainless steel, a pseudo-elastic metal such as a nickel titanium alloy or Nitinol, or a so-called super alloy, which may have a base metal of nickel, cobalt, chromium, or other metal. "Self-expanding" as used herein means that a structure/component has a mechanical memory to return to the expanded or deployed configuration. Mechanical memory may be imparted to the wire or tubular structure that forms stent 102 by thermal treatment to achieve a spring temper in stainless steel, for example, or to set a shape memory in a susceptible metal alloy, such as nitinol, or a polymer, such as any of the polymers disclosed in U.S. Pat. Appl. Pub. No.

2004/0111111 to Lin, which is incorporated by reference herein in its entirety. Alternatively, heart valve prosthesis 100 may be balloon-expandable as would be understood by one of ordinary skill in the art.

Figure 1A:
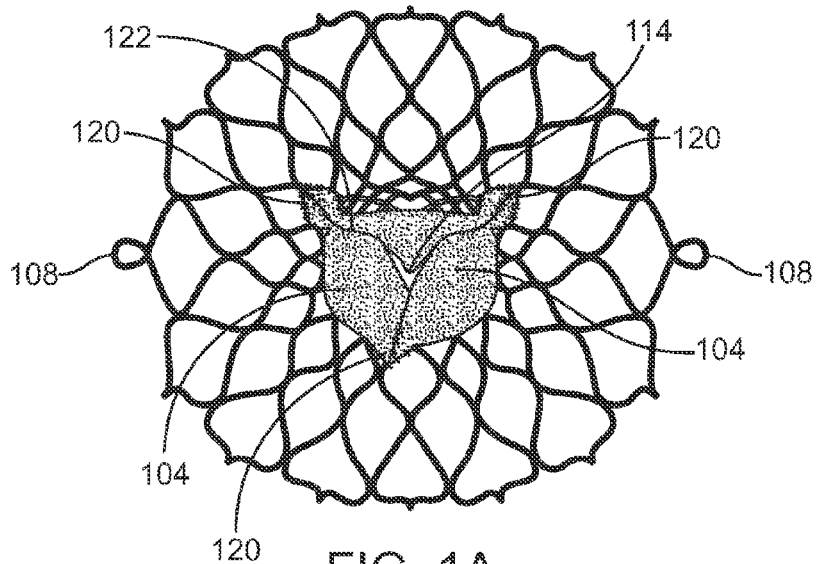
FIG. 1A is a top view illustration of the heart valve prosthesis of FIG. 1.
Figure 1B:
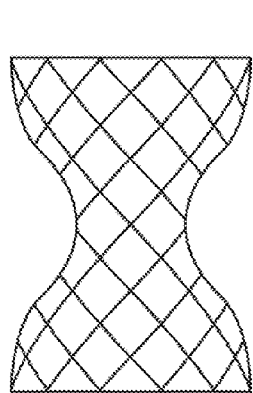
FIG. 1B is a side view illustration of an alternative configuration of a heart valve prosthesis for use in embodiments hereof.
Figure 1C:
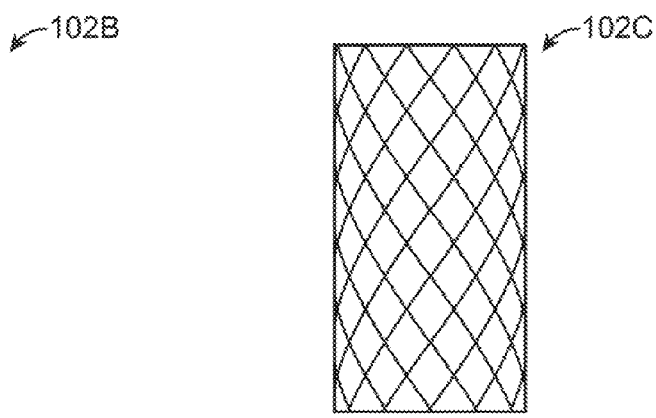
FIG. 1C is a side view illustration of an alternative configuration of a heart valve prosthesis for use in embodiments hereof.

In the embodiment depicted in FIGS. 1 and 1A, stent 102 of valve prosthesis 100 has a deployed configuration including an enlarged first end or section 116, a constriction or waist region 117, and a second end or section 118. Enlarged first section 116 has nominal deployed diameter $D_1$, second section 118 has nominal deployed diameter $D_2$, and constriction region 117 has deployed substantially fixed diameter $D_3$. Each section of stent 102 may be designed with a number of different configurations and sizes to meet the different requirements of the location in which it may be implanted. When configured as a replacement for an aortic valve, second section 118 functions as an inflow end of heart valve prosthesis 100 and extends into and anchors within the aortic annulus of a patient's left ventricle, while first section 116 functions as an outflow end of heart valve prosthesis 100 and is positioned in the patient's ascending aorta. When configured as a replacement for a mitral valve, enlarged first section 116 functions as an inflow end of heart valve prosthesis 100 and is positioned in the patient's left atrium, while second section 118 functions as an outflow end of heart valve prosthesis 100 and extends into and anchors within the mitral annulus of a patient's left ventricle. For example, U.S. Patent Application Publication Nos. 2012/0101572 to Kovalsky et al. and 2012/0035722 to Tuval, each of which are herein incorporated by reference in their entirety, illustrate heart valve prostheses configured for placement in a mitral valve. Each section of stent 102 may have the same or different cross-section which may be for example circular, ellipsoidal, rectangular, hexagonal, rectangular, square, or other polygonal shape, although at present it is believed that circular or ellipsoidal may be preferable when the valve prosthesis is being provided for replacement of the aortic or mitral valve. As alternatives to the deployed configuration of FIGS. 1 and 1A, the stent or valve support frame may have an hourglass configuration 102B shown in FIG. 1B, a generally tubular configuration 102C as shown in FIG. 1C, or other stent configurations or shapes known in the art for valve replacement. Stent 102 also may include eyelets 108 that extend from first end 116 thereof for use in loading the heart valve prosthesis 100 into a delivery catheter (not shown).

As previously mentioned, heart valve prosthesis 100 includes a prosthetic valve component within the interior of stent 102. The prosthetic valve component is capable of blocking flow in one direction to regulate flow there through via valve leaflets 104 that may form a bicuspid or tricuspid replacement valve. FIG. 1A is an end view of FIG. 1 and illustrates an exemplary tricuspid valve having three leaflets 104, although a bicuspid leaflet configuration may alternatively be used in embodiments hereof. More particularly, if heart valve prosthesis 100 is configured for placement within a native valve having three leaflets such as the aortic, tricuspid, or pulmonary valves, heart valve prosthesis 100 includes three valve leaflets 104. If heart valve prosthesis 100 is configured for placement within a native valve having two leaflets such as the mitral valve, heart valve prosthesis 100 includes two valve leaflets 104. Valve leaflets 104 are sutured or otherwise securely and sealingly attached to the interior surface of stent 102 and/or graft material 106 which encloses or lines stent 102 as would be known to one of ordinary skill in the art of prosthetic tissue valve construction. Referring to FIG. 1, leaflets 104 are attached along their bases 110 to graft material 106, for example, using sutures or a suitable biocompatible adhesive. Adjoining pairs of leaflets are attached to one another at their lateral ends to form commissures 120, with free edges 122 of the leaflets forming coaptation edges that meet in area of coaptation 114.

Leaflets 104 may be made of pericardial material; however, the leaflets may instead be made of another material. Natural tissue for replacement valve leaflets may be obtained from, for example, heart valves, aortic roots, aortic walls, aortic leaflets, pericardial tissue, such as pericardial patches, bypass grafts, blood vessels, intestinal submucosal tissue, umbilical tissue and the like from humans or animals. Synthetic materials suitable for use as leaflets 104 include DACRON® polyester commercially available from Invista North America S.A.R.L. of Wilmington, Del., other cloth materials, nylon blends, polymeric materials, and vacuum deposition nitinol fabricated materials. One polymeric material from which the leaflets can be made is an ultra-high molecular weight polyethylene material commercially available under the trade designation DYNEEMA from Royal DSM of the Netherlands. With certain leaflet materials, it may be desirable to coat one or both sides of the leaflet with a material that will prevent or minimize overgrowth. It is further desirable that the leaflet material is durable and not subject to stretching, deforming, or fatigue.

Graft material 106 may also be a natural or biological material such as pericardium or another membranous tissue such as intestinal submucosa. Alternatively, graft material 106 may be a low-porosity woven fabric, such as polyester, Dacron fabric, or PTFE, which creates a one-way fluid passage when attached to the stent. In one embodiment, graft material 106 may be a knit or woven polyester, such as a polyester or PTFE knit, which can be utilized when it is desired to provide a medium for tissue ingrowth and the ability for the fabric to stretch to conform to a curved surface. Polyester velour fabrics may alternatively be used, such as when it is desired to provide a medium for tissue ingrowth on one side and a smooth surface on the other side. These and other appropriate cardiovascular fabrics are commercially available from Bard Peripheral Vascular, Inc. of Tempe, Ariz., for example.

Delivery of heart valve prosthesis 100 may be accomplished via a percutaneous transfemoral approach. During delivery, the prosthetic valve remains compressed until it reaches a target diseased native heart valve, at which time the heart valve prosthesis 100 can be released from the delivery catheter and expanded in situ via self-expansion. The delivery catheter is then removed and heart valve prosthesis 100 remains deployed within the native target heart valve.

Figure 2:
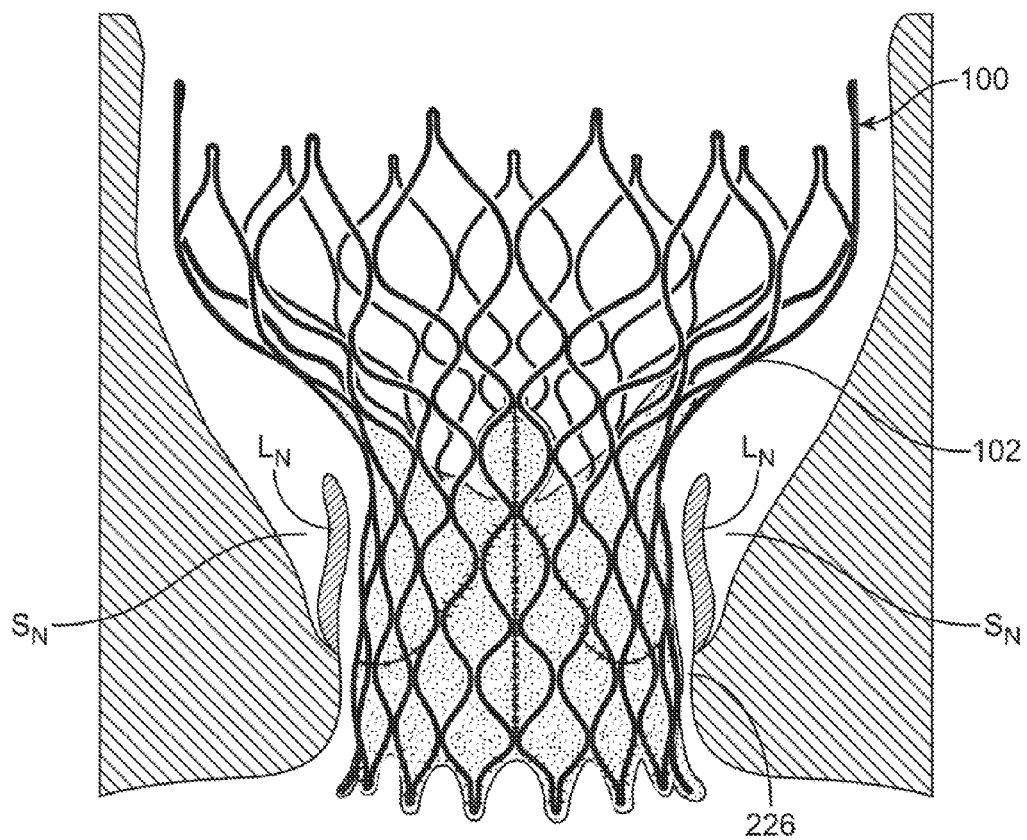
FIG. 2 is a side view illustration of the heart valve prosthesis of FIG. 1 implanted within a native valve annulus.

FIG. 2 is a side view illustration of heart valve prosthesis 100 implanted within a native heart valve, which is shown in section, having native leaflets $L_N$ and corresponding native sinuses $S_N$. When heart valve prosthesis 100 is deployed within the valve annulus of a native heart valve, stent 102 expands within native valve leaflets $L_N$ of the patient's defective valve, retaining the native valve leaflets in a permanently open state. The native valve annulus may include surface irregularities on the inner surface thereof, and as a result one or more gaps or crevices 226 may be present or may form between the perimeter of heart valve prosthesis 100 and the native valve annulus. For example, calcium deposits may be present on the native valve leaflets (e.g., stenotic valve leaflets) and/or shape differences may be present between the native heart valve annulus and prosthesis 100. More particularly, in some cases native annuli are not perfectly rounded and have indentations corresponding to the commissural points of the native valve leaflets. As a result, a prosthesis having an approximately circular shape does not provide an exact fit in a native valve. These surface irregularities, whatever their underlying cause, can make it difficult for conventional prosthetic valves to form a blood tight seal between the prosthetic valve and the inner surface of the valve annulus, causing undesirable paravalvular leakage and/or regurgitation at the implantation site.

Figure 3:
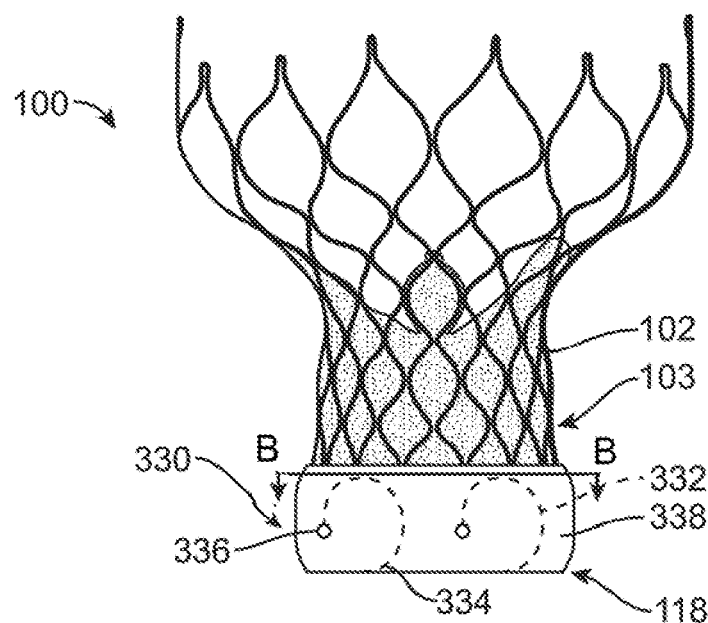
FIG. 3 is a side view of the heart valve prosthesis of FIG. 1 having an anti-paravalvular leakage component coupled thereto, wherein the anti-paravalvular leakage component includes a plurality of struts and an annular sealing membrane coupled to the struts and the heart valve prosthesis and the anti-paravalvular leakage component are both in deployed configurations.

Embodiments hereof relate to methods for delivering a heart valve prosthesis having a self-expanding anti-paravalvular leakage component thereon that functions to occlude or fill gaps between the perimeter of a heart valve prosthesis and the native valve annulus, thereby reducing, minimizing, or eliminating leaks there through. An anti-paravalvular leakage component 330 is shown in FIG. 3 in its deployed or expanded configuration, extending around an outer surface or perimeter 103 of stent 102 of heart valve prosthesis 100 adjacent to second or distal end 118 thereof to prevent paravalvular leakage in situ. When deployed, anti-paravalvular leakage component 330 may be positioned in situ at the native valve annulus, slightly above the valve annulus, slightly below the valve annulus, or some combination thereof, and functions to substantially fill gaps or cavities or crevices between outer surface 103 of stent 102 and native valve tissue. "Substantially fill" as utilized herein means that blood flow through the target gap or cavity is occluded or blocked, or stated another way blood is not permitted to flow there through. In the deployed configuration, anti-paravalvular leakage component 330 is in apposition with the native valve annulus and blocks blood flow around the outer perimeter of prosthesis 100, thereby minimizing and/or eliminating any paravalvular leakage at the implantation site and providing hemostasis around the prosthesis. Although embodiments depicted herein illustrate an anti-paravalvular leakage component integrated onto a heart valve prosthesis configured for implantation within an aortic valve, one of ordinary skill in the art would understand that an anti-paravalvular leakage component as described herein may be integrated onto a heart valve prosthesis configured for implantation within other heart valves such as but not limited to the mitral valve.

More particularly, anti-paravalvular leakage component 330 includes a plurality of independent, self-expanding segments or struts 332 and an annular sealing membrane 338 coupled to struts 332. Each strut 332 is a filament or strand structure having a first end 334 coupled to second end 118 of prosthesis 100 and a second or free end 336 that is not coupled to prosthesis 100. Although not required, second or free end 336 may include eyelets as an option for attachment of annular sealing membrane 338. First end 334 of strut 332 may be coupled to outer surface 103 of stent 102 via welding, sutures, or other suitable mechanical method. In another embodiment hereof, strut 332 may be integrally formed with stent 102 of heart valve prosthesis 100. Regardless of whether anti-paravalvular leakage component 330 is formed concurrently with or subsequent to heart valve prosthesis 100, struts 332 of anti-paravalvular leakage component 330 are each formed from filament or strand structure that may be solid or hollow and may have a different cross-section and/or size from stent 102 of heart valve prosthesis 100. More particularly, in an embodiment, stent 102 is formed via laser-cut manufacturing method and therefore a segment of the stent may have a non-circular cross-section, e.g., a square, rectangular, or polygonal cross-section, and a thickness ranging between 0.005-0.030 inches, depending in part upon the material thereof. Struts 332 may be formed from a filament or strand structure having a circular or round cross-section with a diameter between 0.005-0.030 inches, depending in part upon the material thereof. In another embodiment, the cross-section of strut 332 may be an oval, elliptical, rectangular or ribbon-like, or any other suitable shape. By forming struts 332 of a relatively thinner or smaller filament or strand structure as compared to a segment of stent 102, struts 332 have greater flexibility to conform to the inner surface of the native valve annulus including any surface irregularities that may be present, thereby filling gaps or cavities or crevices that may be present between the heart valve prosthesis 100 and native tissue, while the thicker segments of stent 102 provide sufficient radial force to deploy the heart valve prosthesis into apposition with the native valve annulus. In another embodiment hereof, struts 332 may be integrally formed with stent 102 of heart valve prosthesis via a laser-cut manufacturing method. If integrally formed with stent 102, the cross-section of struts 332 may be the same size and shape as a segment of the stent or may be of a different size and/or shape as a segment of the stent.

Figure 4A:
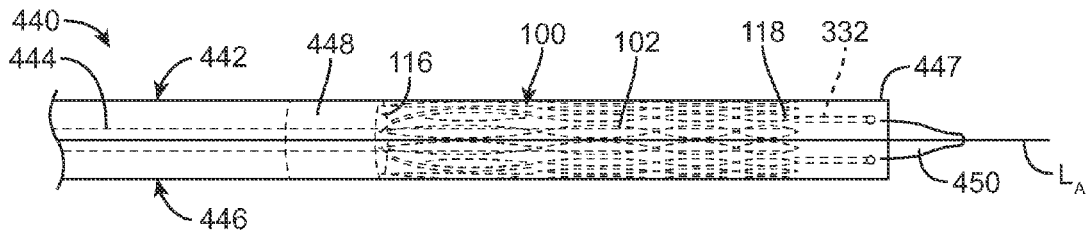
FIG. 4A illustrates a side view of the heart valve prosthesis of FIG. 3 in a delivery or compressed configuration, loaded into a delivery system, according to an embodiment hereof, wherein a sealing membrane of the anti-paravalvular leakage component are not shown for illustrative purposes.
Figure 4B:
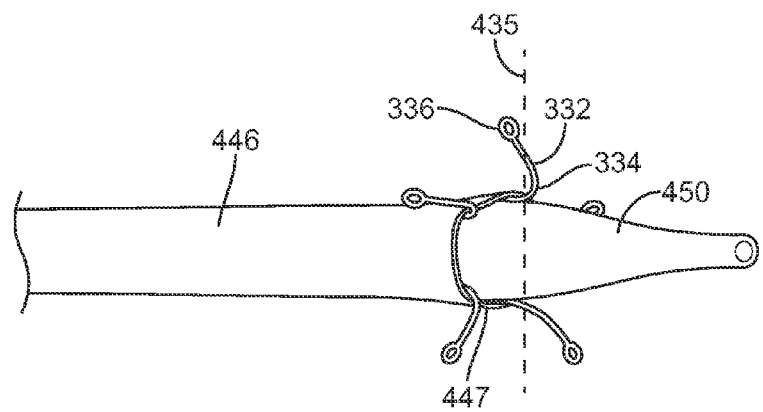
FIGS. 4B-4D illustrate side and end views of the valve prosthesis of FIG. 4A, wherein a sheath of the delivery system is progressively retracted to expose and release the struts of the anti-paravalvular leakage component.
Figure 4C:
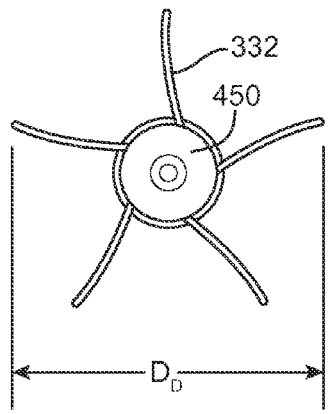

Struts 332 are spaced apart in approximately equal intervals or distances around heart valve prosthesis 100, as shown in FIGS. 4B and 4C described herein. Although shown with five struts 332, it will be understood by one of ordinary skill in the art that a greater or lesser number of segments may be utilized herein. In another embodiment hereof (not shown) struts 332 may be spaced apart in non-equal intervals or distances around the outside of the heart valve prosthesis. For example, it may be desirable to position one or more segments at a location on the heart valve prosthesis corresponding to an area prone to leakage in situ, such as adjacent to the native valve commissures.

As will be explained in more detail herein, anti-paravalvular leakage component 330 is moveable between a compressed configuration and a deployed configuration. In the compressed or delivery configuration, each strut 332 distally extends from the distal or second end 118 of prosthesis 100. During deployment, each strut 332 bends more than ninety degrees with respect to its compressed, delivery configuration during deployment of valve prosthesis 100. In one embodiment, each strut 332 bends between 140 degrees and 180 degrees during deployment of valve prosthesis 100. When released from an outer sheath or cover (not shown in FIG. 3), each strut 332 bends outwardly and proximally, and rotates or twists towards an outer surface of the delivery device or stent until it reaches its deployed configuration of FIG. 3 in which each strut 332 has a C-shape that extends proximally away from the distal or second end 118 of prosthesis 100 and is oriented substantially flush with outer surface 103 of stent 102. As utilized here, "substantially flush" includes struts that are lying flat, level, or in plane with and abutting against the outer surface of stent 102 as well as struts that are flat, level, or in plane tangential to outer surface 103 of stent 102 but slightly spaced apart therefrom, i.e., less than six millimeters therefrom. As utilized herein, "tangential" includes struts in which the C-shape lies in a plane tangential to the outer surface 103 of the stent 102 or in which the plane in which the C-shape lies is offset ten degrees or less with a plane tangential to outer surface 103 of stent 102. In order to transform between the initial distally-extending compressed configuration and the final proximally-extending deployed configuration, struts 332 of anti-paravalvular leakage component 330 are formed from a self-expanding material that has a mechanical memory to return to their preset proximally-extending deployed or preset expanded configuration. Struts 332 may be made from a metallic material having a mechanical memory to return to the deployed or preset expanded configuration. Mechanical memory may be imparted to struts 332 by thermal treatment to achieve a spring temper in stainless steel, for example, or to set a shape memory in a susceptible metal alloy, such as NiTi (Nitinol) or Co—Cr (Cobalt-Chrome). In an alternate embodiment, a mechanical memory to return to deployed or preset expanded configuration may be imparted to a shape memory polymer that forms struts 332, such as any of the polymers disclosed in U.S. Pat. Appl. Pub. No. 2004/0111111 to Lin, which is herein incorporated by reference in its entirety.

Annular sealing skirt or membrane 338 is coupled to struts 332. In an embodiment hereof, annular sealing membrane 338 may be formed from a swellable material that collapses easily and expands to a larger volume after implantation, such as but not limited to hydrogel or a collagen foam/sponge similar to the material commercially available under the trademark Angioseal. Other suitable material examples for annular sealing membrane 338 include tissue, compressible foam materials, compressible polymeric materials, or a low-porosity knit or woven fabric, such as polyester, Dacron fabric, or PTFE. Porous materials advantageously provide a medium for tissue ingrowth and have the ability to stretch to conform to a curved surface. Polyester velour fabrics may alternatively be used, such as when it is desired to provide a medium for tissue ingrowth on one side and a smooth surface on the other side. Sealing membrane 338 may include one or more of the above-listed materials, such as but not limited to a combination of foam, fabric, and/or tissue.

Figure 3B:
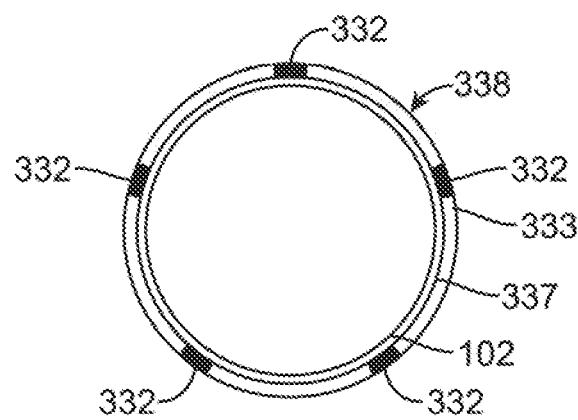
FIG. 3B is a cross-sectional view taken along line B-B of FIG. 3.

In the embodiment of FIG. 3 and FIG. 3B, sealing membrane 338 includes two layers, a first layer 337 coupled to an inner surface of struts 332 and a second layer 333 coupled to an outer surface of struts 332, thereby sandwiching struts 332 between the two layers of sealing material and allowing for more material (as compared to a single layer) to prevent leakage. In addition, when deployed, the presence of sealing material between struts 332 and stent 102 prevents the struts and the stent from rubbing or fretting against each other. It will be understood by those of ordinary skill in the art that the cross-sectional view of FIG. 3B illustrates slight spaces or gaps between first and second layers 337, 333 of sealing material, as well as between first layer 337 and stent 102, for illustrative purposes only. When deployed in situ, the two layers of sealing material, as well as the first layer 337 and stent 102, may contact and abut against each other. The first and second layers of sealing membrane 338 may be of the same material or may be different materials, such as but not limited to a combination of tissue and fabric or a combination of two different tissues such as bovine tissue and porcine tissue. The first and second layers of sealing membrane 338 may be coupled to struts 332 via sutures or other suitable mechanical connection. If formed from the same material, the first and second layers may be integrally formed and placed over struts 332 such that there is no seam between therebetween in order to minimize the packing density thereof.

In another embodiment (not shown), sealing membrane 338 may include a single layer coupled to an inner surface of struts 332 when struts 332 are in the deployed configuration or may include a single layer coupled to an outer surface of struts 332 when struts 332 are in the deployed configuration.

In one embodiment shown in FIG. 3, the length or diameter of sealing membrane 338 is approximately equal to or only slightly greater, i.e., up to 10% greater, than the expanded outer diameter of stent 102. When struts 332 radially expand or deploy as described in more detail herein, annular sealing membrane 338 is positioned around the outer surface or perimeter of heart valve prosthesis 100. As will be described in more detail herein, struts 332 bend or flip backward and twist during deployment thereof. Since anti-paravalvular leakage component 330 is sized to seal on a fully expanded heart valve prosthesis and is initially compressed or constrained in a delivery configuration, sealing membrane 338 has sufficient material or slack to bend or flip backward and twist into the deployed configuration with struts 332. In addition, depending upon the material of sealing membrane 338, the sealing membrane may be formed from a stretchable and resilient material which aids in the deployment thereof. When deployed, annular sealing membrane 338 extends into and substantially fills gaps or cavities or crevices between outer surface 103 of stent 102 and native valve tissue to prevent paravalvular leakage in situ. In another embodiment hereof shown in FIG. 3A, the length or diameter of a sealing membrane 338A is between 10% and 50% greater than the expanded outer diameter of stent 102. As such, the material of sealing membrane 338A bunches or billows in regions 339 between adjacent struts 332A, with the amount of bunching depending upon both the length or diameter of sealing membrane 338A as well as the height or length of the struts attached thereto. The excess or slack material of regions 339 may further extends into and substantially fill gaps or cavities or crevices between outer surface 103 of stent 102 and native valve tissue to prevent paravalvular leakage in situ.

Deployment of anti-paravalvular leakage component 330 from the compressed or delivery configuration to the expanded or deployed configuration will now be discussed with reference to FIGS. 4A-4K. For illustrative purposes, annular sealing membrane 338 is removed from FIGS. 4A-4K so that the transformation of struts 332 may be clearly shown. Although deployment of struts 332 is described in several steps or stages, it will be understood by those of ordinary skill in the art that the transition between the delivery configuration to the fully deployed configuration is a continuous smooth movement or stroke. FIG. 4A illustrates a side view of valve prosthesis 100 in an compressed or delivery configuration sized for delivery to the target site, loaded into a delivery system 440. Delivery system 440 includes a catheter 442, which includes inner shaft 444 and an outer retractable sheath or cover 446 slidingly disposed over inner shaft 444. Valve prosthesis 100 is mounted over inner shaft 444 of catheter 442 at the distal end thereof and sheath 446, which has a distal end 447, surrounds and constrains valve prosthesis 100 in the compressed configuration. A tapered flexible nosecone or tip 450 is coupled to a distal end of inner shaft 444. In one embodiment, catheter 442 may also include a retainer 448 which temporarily secures proximal or first end 116 of stent 102 onto catheter 442. For example, retainer 448 may include an end stent capture configuration as described in U.S. Patent Pub. 2009/0276027 to Glynn, which is hereby incorporated by reference herein in its entirety. In the compressed or delivery configuration, each strut 332 is straightened or substantially straightened and extends distally from distal or second end 118 of stent 102. "Substantially straightened" as used herein includes struts that extend parallel with a longitudinal axis $L_A$ of stent 102. By straightening and extends distally from distal or second end 118 of stent 102, struts 332 and therefore anti-paravalvular leakage component 330 approach a substantially linear delivery configuration within the outer sheath. Although not shown in FIG. 4A, annular sealing membrane 338 packs or compresses within and between compressed struts 332 during delivery thereof. Accordingly, anti-paravalvular leakage component 330 advantageously does not increase, or minimally increases, the packing profile of heart valve prosthesis 100 so that heart valve prosthesis 100 has the ability to pack in lower profile delivery systems.

In order to begin deployment of valve prosthesis 100, sheath 446 is retracted in a proximal direction to expose and release second ends 336 of struts 332 as shown in the side view of FIG. 4B and the end view of FIG. 4C. Upon initial release from sheath 446, second ends 336 of struts 332 flare or spread radially away from delivery system 440. At this stage of deployment, struts 332 begin to bend or curve backwards. FIG. 4B includes a transverse reference axis 435, which as utilized herein describes an imaginary reference line that extends approximately ninety degrees or perpendicular to the longitudinal axis $L_A$ of stent 102. One particular feature of struts 332 is apparent in FIG. 4B which illustrates second ends 336 of struts 332 passing over transverse reference axis 435. Struts 332 bend or curve backwards such that second or free ends 336 of struts 332 pass or bend over the transverse reference axis 435 before first or attached ends 334 of struts 332. Since struts 332 are curved or bent in this manner, a deployment diameter $D_D$ of struts 332 is reduced or minimized as compared to if the struts were straight and extended generally perpendicular to the longitudinal axis $L_A$ of stent 102 during deployment, i.e., if both ends 334, 336 of struts 332 crossed over the transverse reference axis 435 at the same time. In other words, struts 332 bend or curve along the length thereof, as opposed to bending only at a hinge point near end 334. Thus, when end 334 is generally perpendicular to longitudinal axis $L_A$, strut 332 is curved rather than being straight, thereby minimizing the deployment diameter $D_D$ of struts 332. For example, deployment diameter $D_D$ of struts 332 may be between 18 and 22 mm and in one embodiment may be 20 mm. Minimization of deployment diameter $D_D$ is advantageous in order to minimize interference with surrounding tissue of the native valve during deployment of valve prosthesis 100.

Figure 4D:
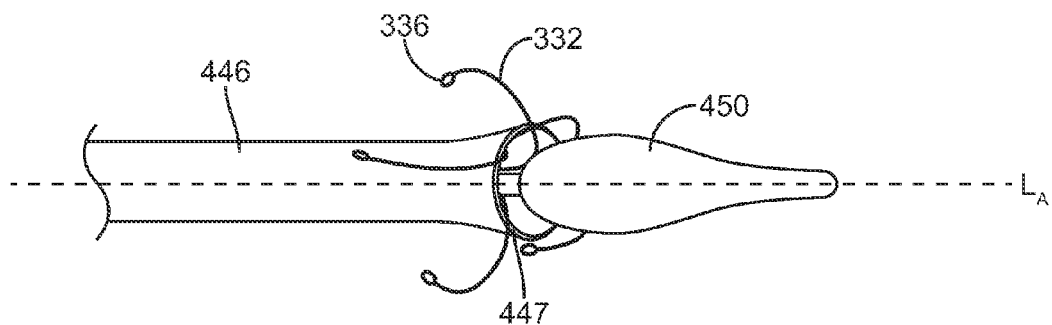

As sheath 446 is further retracted, struts 332 continue to be exposed and continue to bend or flip backwards towards the outer surface of sheath 446 and stent 102 compressed therein until the struts 332 are fully exposed or released from sheath 446 and are generally C-shaped as shown in FIG. 4D. Notably, as struts 332 are released from sheath 446, stent 102 remains constrained within sheath 446. In this partially deployed stage or configuration, each strut 332 is oriented within a plane through the longitudinal axis $L_A$ of stent 102. Stated another way, the C-shape of each strut is oriented in a radially outward direction with respect to sheath 446 and stent 102.

Figure 3A:
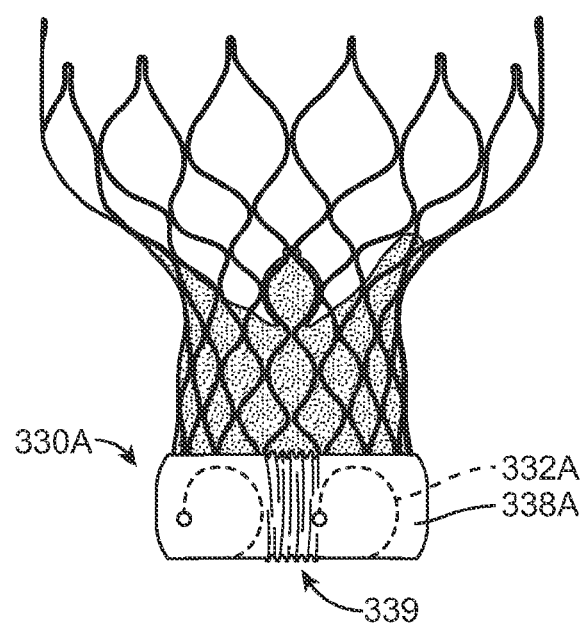
FIG. 3A is a side view of the heart valve prosthesis of FIG. 1 having another anti-paravalvular leakage component coupled thereto, wherein an annular sealing membrane of the anti-paravalvular leakage component billows or bunches between struts of the anti-paravalvular leakage component.
Figure 4E:
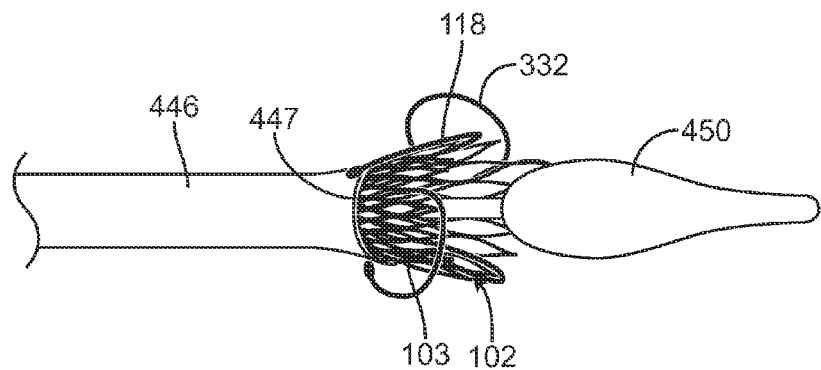
FIGS. 4E-4G illustrate side views of the valve prosthesis of FIG. 4A, wherein a sheath of the delivery system is progressively retracted to expose and release a distal end of the stent of the valve prosthesis.
Figure 4F:
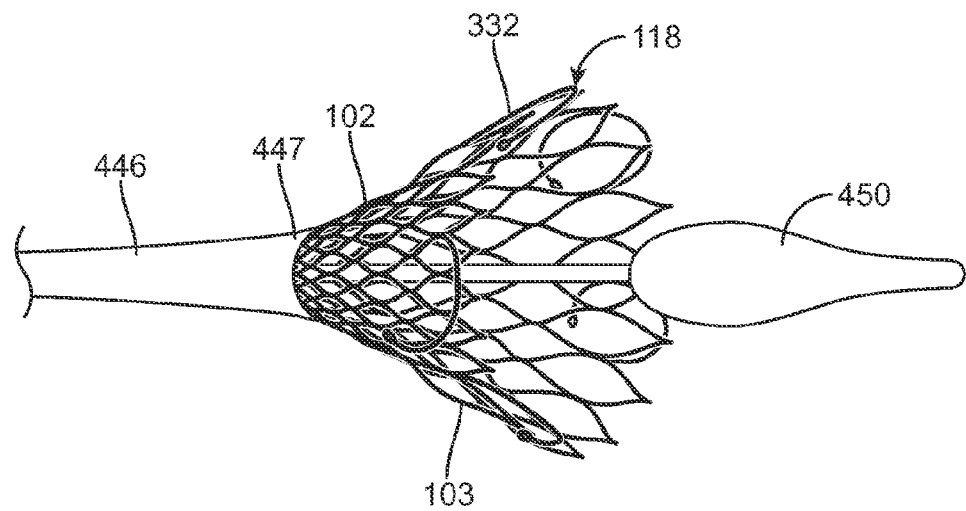
Figure 4G:
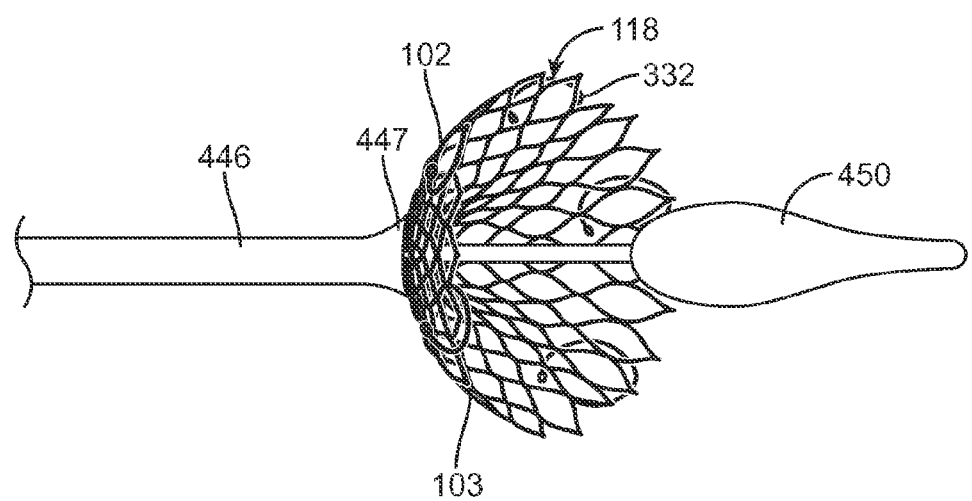

FIGS. 4E and 4F illustrate the continued deployment of valve prosthesis 100. Sheath 446 continues to be proximally retracted, exposing second or distal end 118 of self-expanding stent 102 such that stent 102 is released to assume its deployed configuration. As can be seen in a comparison of FIG. 4E and FIG. 4F, as distal end 118 of stent 102 expands, each C-shaped strut 332 rotates, twists, or turns such that the C-shape is oriented within a plane taken along the outer surface 103 of stent 102. In other words, C-shaped strut 322 lies in a plane that is generally tangential to other surface 103 of stent 102 or parallel to and slightly spaced from such a plane. As can be seen in FIGS. 3, 3A, and 4G, the C-shape of the strut 322 is seen when view the stent in the plane described above. Stated another way, the C-shape of strut 322 is seen in a side view of the stent valve prosthesis 100.

FIG. 4G illustrates second or distal end 118 of self-expanding stent 102 fully expanded with the final deployed configuration of struts 332, in which each strut 332 extends proximally from distal or second end 118 of stent 102. The backwards bending or flipping that occurs during deployment results in each strut 332 translating more than ninety degrees from its compressed, delivery configuration. During deployment, each strut 332 essentially deploys or translates in an arc path that extends between 90 and 180 degrees from the initial compressed configuration and the final deployed configuration. In addition to bending backwards, struts 332 also rotate or twist so that its C-shape is oriented substantially flush with outer surface 103 of stent 102 when strut 332 is in its final deployed configuration. Comparing FIG. 4D and FIG. 4G, each strut 332 rotates or twists from the partially deployed stage or configuration in which it is oriented within a plane taken through the longitudinal axis $L_A$ of stent 102 to the final deployed stage or configuration in which the C-shape is oriented within a plane taken along or tangential to the outer surface 103 of stent 102.

Figure 4H:
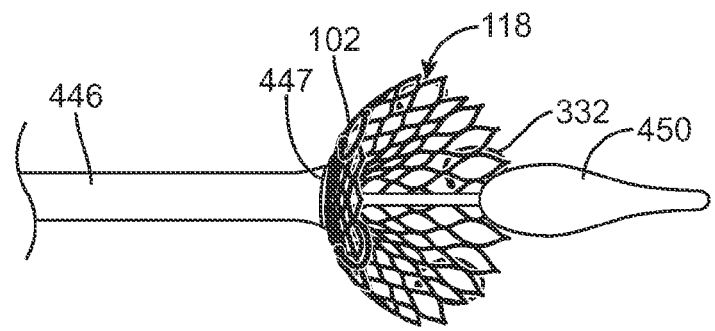
FIGS. 4H-4I illustrate side views of the valve prosthesis of FIG. 4A, wherein a sheath of the delivery system is progressively distally advanced to recapture the distal end of the stent of the valve prosthesis.
Figure 4I:
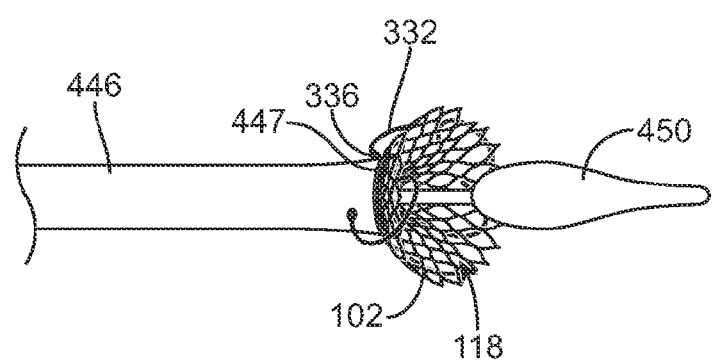
Figure 4J:
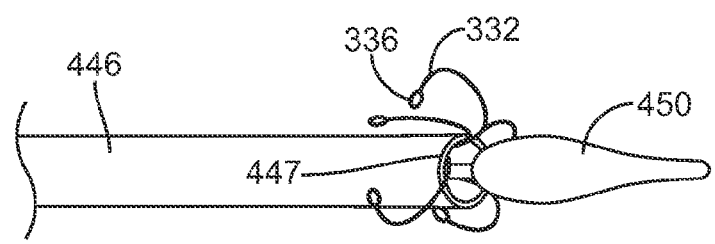
FIGS. 4J-4K illustrate side views of the valve prosthesis of FIG. 4A, wherein a sheath of the delivery system is progressively distally advanced to recapture the struts of the anti-paravalvular leakage component.
Figure 4K:
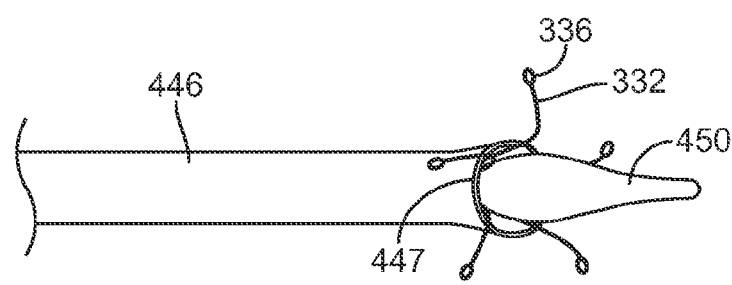

At this stage of deployment, sheath 446 may be proximally retracted until proximal or first end 116 of stent 102 is exposed and allowed to self-expand, thereby uncoupling from retaining tip 448 of catheter 442. However, if any repositioning is desired, sheath 446 may alternatively be distally advanced to recapture struts 332 and distal or second end 118 of stent 102. More particularly, recapture of struts 332 and distal or second end 118 of stent 102 is shown and described with reference to FIGS. 4H-4K. In FIGS. 4H and 4I, sheath 446 is distally advanced over distal or second end 118 of stent 102 until the stent is fully constrained within the sheath as shown in FIG. 4J. Struts 332 are not yet recaptured, but distal advancement of sheath 446 causes struts 332 to rotate or turn back to the partially deployed configuration in which each C-shaped strut 332 is oriented within a plane taken through the longitudinal axis $L_A$ of stent 102. Further distal advancement of sheath 446 results in recapture of struts 332, with second ends 336 of struts 332 exposed and spread radially away from delivery system 440. At this stage of recapture, struts 332 bend or curve gradually backwards but are no longer C-shaped. Stent 102, which is recaptured within sheath 446, may be repositioned as desired.

Figure 5A:
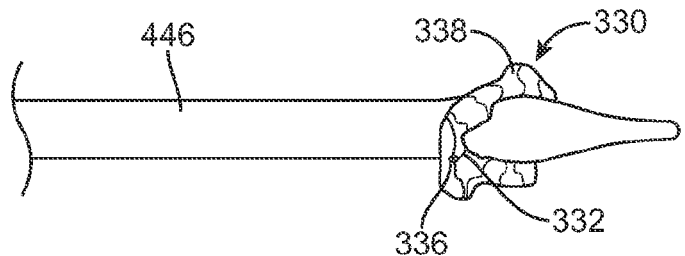
FIGS. 5A-5D illustrate the progressive deployment of the heart valve prosthesis of FIG. 3, wherein an annular sealing membrane of the anti-paravalvular leakage component is shown.
Figure 5B:
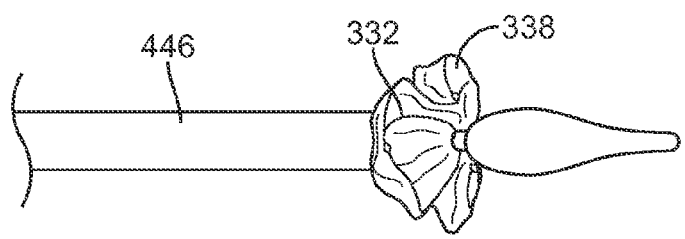

FIGS. 5A-5D illustrate the progressive deployment of anti-paravalvular leakage component 330 having an annular sealing membrane 338 coupled to struts 332. Sheath 446 is retracted in a proximal direction to expose and release a distal end of anti-paravalvular leakage component 330 as shown in the side view of FIG. 5A. Upon initial release from sheath 446, second or free ends 336 of struts 332 bend or curve gradually backwards as described above with respect to FIGS. 4B and 4C. Sealing membrane 338 radially expands or bulges outward when struts 332 are released from sheath 446. As sheath 446 is further retracted, anti-paravalvular leakage component 330 continue to be exposed and struts 332 continue to bend backwards towards the outer surface of sheath 446 and stent 102 compressed therein until the struts 332 are fully exposed or released from sheath 446 and are generally C-shaped as shown in FIG. 5B. At this stage of deployment, the C-shape of each strut is oriented in a radially outward direction with respect to sheath 446 and stent 102 as described above with respect to FIG. 4D. Since struts 332 bend backwards, sealing membrane 338 of anti-paravalvular leakage component 330 is now positioned on the outer surface of struts 332. Stated another way, since struts 332 flip over or evert during deployment, sealing membrane 338 is positioned on an outer surface of anti-paravalvular leakage component 330 when in the deployed or partially deployed configuration.

Figure 5C:
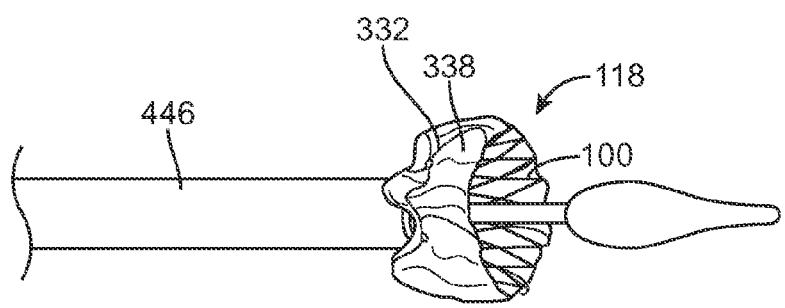
Figure 5D:
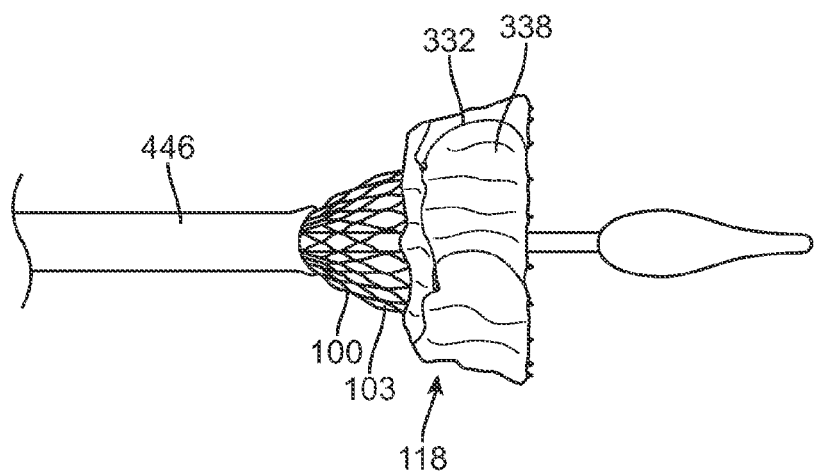

Sheath 446 continues to be proximally retracted, exposing second or distal end 118 of self-expanding stent 102 such that stent 102 is released to assume its deployed configuration. As distal end 118 of stent 102 expands, each C-shaped strut 332 rotates, twists, or turns such that the C-shape is oriented within a plane taken along the outer surface of stent 102 as shown in FIG. 5C. FIG. 5D illustrates second or distal end 118 of self-expanding stent 102 fully expanded with the final deployed configuration of struts 332, in which each strut 332 extends proximally from distal or second end 118 of stent 102 and the C-shape of each strut 332 is oriented substantially flush with outer surface 103 of stent 102. Sealing membrane 338 extends between adjacent struts 332 and extends into and substantially fill gaps or cavities or crevices between outer surface 103 of stent 102 and native valve tissue to prevent paravalvular leakage in situ.

Figure 6A:
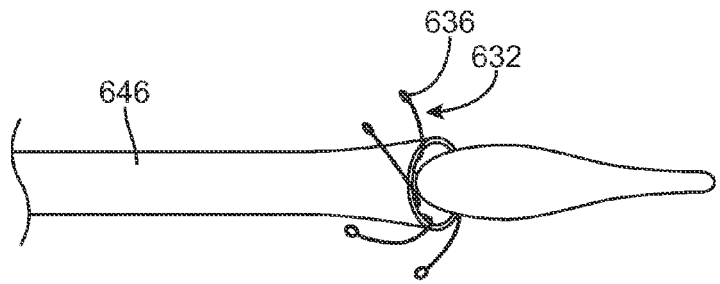
FIGS. 6A-6C illustrate side and end views of the heart valve prosthesis of FIG. 1 having another embodiment of an anti-paravalvular leakage component coupled thereto, wherein a sheath of a delivery system is progressively retracted to expose and release struts of the anti-paravalvular leakage component.
Figure 6B:
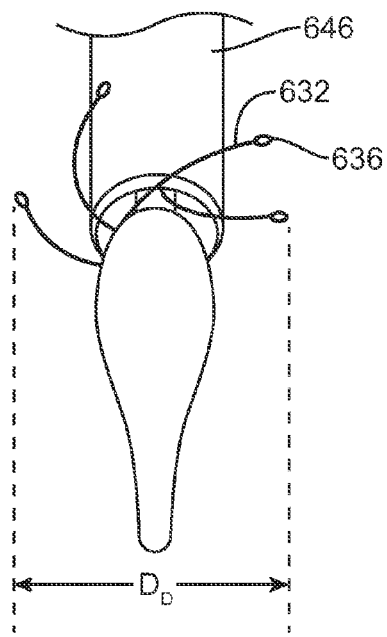
Figure 6C:
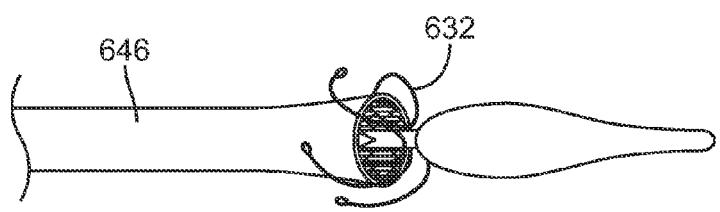

FIGS. 6A-6C illustrate another embodiment hereof in which struts 632 of an anti-paravalvular leakage component spiral or circumferentially curve around the outer sheath during deployment thereof. For illustrative purposes, the annular sealing membrane of the anti-paravalvular leakage component is not shown so that the transformation of struts 632 may be clearly shown. In order to begin deployment of a valve prosthesis, which is obscured from view in FIGS. 6A-6C since it is contained within an outer sheath 646, sheath 646 is retracted in a proximal direction to expose and release second ends 636 of struts 632 as shown in the side view of FIG. 6A and the end view of FIG. 6B. Upon initial release from sheath 646, second or free ends 636 of struts 632 flare or spread radially away from the delivery system. At this stage of deployment, struts 632 bend or curve gradually backwards. In addition to bending or curving backwards, struts 632 also bend or curve around sheath 646 in a circumferential direction. Due to the curvature of struts 632, a deployment diameter $D_D$ of struts 632 is reduced or minimized to between 13 and 17 mm and in one embodiment may be 15 mm. Minimization of deployment diameter $D_D$ is advantageous in order to minimize interference with surrounding tissue of the native valve during deployment of valve prosthesis 100.

As sheath 646 is further retracted, struts 632 continue to be exposed and continue to bend backwards towards and circumferentially curve around the outer surface of sheath 646 until the struts 632 are fully exposed or released from sheath 646 as shown in FIG. 6C. Notably, as struts 632 are released from sheath 646, the stent remains constrained within sheath 646. Similar to struts 332, struts 632 are C-shaped when deployed. However, in this partially deployed stage or configuration, rather than being oriented within a plane taken through the longitudinal axis $L_A$ of the stent such as struts 332 described above, the C-shape of struts 632 extends circumferentially around at least a portion of the sheath 646 and the stent compressed therein as shown in FIG. 6C. However, similar to struts 332, as the distal end of the stent expands and struts 632 assume their final deployed configuration, struts 632 are oriented substantially flush with the outer surface of the stent. Stated another way, struts 632 have the same finally deployed configuration as struts 332 although struts 632 take or travel a different path during deployment thereof.

Figure 7:
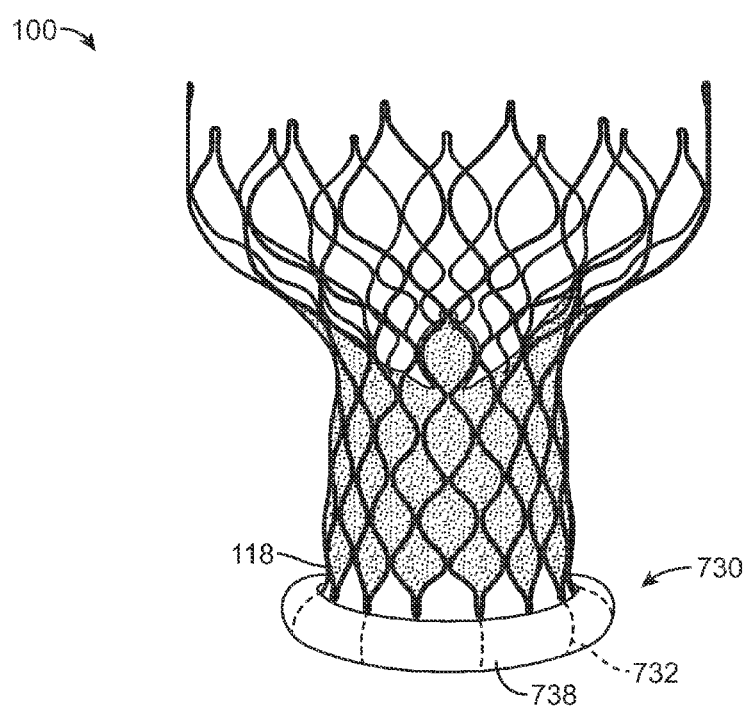
FIG. 7 is a side view of the heart valve prosthesis of FIG. 1 having an anti-paravalvular leakage component according to another embodiment coupled thereto, wherein the anti-paravalvular leakage component includes a plurality of struts and an annular sealing membrane coupled to the struts and the heart valve prosthesis and the anti-paravalvular leakage component are both in deployed configurations.

Turning now to FIG. 7, heart valve prosthesis 100 is shown with another embodiment of an anti-paravalvular leakage component 730 which has a different deployed configuration than anti-paravalvular leakage component 330. More particularly, anti-paravalvular leakage component 730 includes a plurality of independent, self-expanding segments or struts 732 and an annular sealing membrane 738 coupled to struts 732. In this embodiment, sealing membrane 738 is a single layer of material coupled to an inner surface of struts 732 when struts 732 are in the compressed or delivery configuration but may be a double layer of material or may be a single layer coupled to the opposing surface of struts 732 as described above with respect to sealing membrane 338. Similar to struts 332, each strut 732 is a filament or strand structure formed from a self-expanding material that has a mechanical memory to return to its preset proximally-extending deployed or expanded configuration. With additional reference to FIG. 8B, a first end 734 of each strut 732 is coupled to second end 118 of prosthesis 100 and a second or free end 736 of each strut 732 is not coupled to prosthesis 100. In the compressed or delivery configuration, each strut 732 extends distally away from the distal or second end 118 of prosthesis 100 and extends generally parallel to a longitudinal axis of the stent. However, unlike struts 332, each strut 732 has a rolled-up or coiled deployed configuration rather than a C-shape deployed configuration.

The deployment of anti-paravalvular leakage component 730 from the compressed or delivery configuration to the expanded or deployed configuration is shown in FIGS. 8A-8F. FIG. 8A illustrates a side view of valve prosthesis 100 in an compressed or delivery configuration sized for delivery to the target site, loaded into a delivery system 840, with FIG. 8B being a sectional view taken along line B-B of FIG. 8A. Delivery system 840 includes a catheter 842 (shown in FIG. 8D), which includes an inner shaft 844 (also shown in FIG. 8D) and an outer retractable sheath or cover 846 slidingly disposed over inner shaft 844. Valve prosthesis 100 is mounted over inner shaft 844 of catheter 842 at the distal end thereof and sheath 846, which has a distal end 847, surrounds and constrains valve prosthesis 100 in the compressed configuration. A tapered flexible nosecone or tip 850 is coupled to a distal end of inner shaft 844. In the compressed or delivery configuration, each strut 732 is straightened or substantially straightened and extends distally from distal or second end 118 of stent 102. In the compressed configuration, each strut 732 extends generally parallel with a longitudinal axis $L_A$ of stent 102. By straightening and extending distally from distal or second end 118 of stent 102, struts 732 and therefore anti-paravalvular leakage component 730 approach a substantially linear delivery configuration within the outer sheath. Annular sealing membrane 738 packs or compresses within and between compressed struts 732 during delivery thereof. Accordingly, anti-paravalvular leakage component 730 advantageously does not increase, or minimally increases, the packing profile of heart valve prosthesis 100 so that heart valve prosthesis 100 has the ability to pack in lower profile delivery systems.

In order to begin deployment of valve prosthesis 100, sheath 846 is retracted in a proximal direction to expose and release second ends 736 of struts 732 as shown in the side view of FIG. 8C. Upon initial release from sheath 846, second ends 736 of struts 732 flare or spread radially away from delivery system 840. At this stage of deployment, struts 732 bend or curve gradually backwards. As sheath 846 is further retracted, struts 732 continue to be exposed such that second ends 736 of struts 732 roll up or curl upon themselves towards first ends 734, similar to a rolled up stocking or sock. Sheath 846 is retracted until the struts 732 are fully exposed or released from sheath 846 and is rolled-up or coiled in the deployed configuration of anti-paravalvular leakage component 730 as shown in FIGS. 8D-8F. Notably, as struts 732 are released from sheath 846, stent 102 remains constrained within sheath 846 as shown in the sectional view of FIG. 8E which is taken along line E-E of FIG. 8D. FIG. 8F is a cross-sectional view of anti-paravalvular leakage component 730, taken along line F-F of FIG. 8D, and illustrates the rolled-up or coiled deployed configuration of anti-paravalvular leakage component 730. In the deployed configuration, anti-paravalvular leakage component 730 extends radially away from the distal end of the stent. When rolled-up or coiled, each strut 732 rolls at least one full or complete turn or revolution, i.e., at least 360 degrees. Stated another way, when released from sheath 846, second ends 736 of struts 732 turn at least 360 degrees towards sheath 846 and valve prosthesis 100. As shown in FIG. 8F, struts 732 may roll up multiple turns or revolutions. In FIG. 8F, struts 732 are rolled more than two complete revolutions but struts 732 may be rolled up to ten complete turns or revolutions.

At this stage of deployment, sheath 846 may be proximally retracted until proximal or first end 116 of stent 102 is exposed and allowed to self-expand. However, if any repositioning is desired, sheath 846 may alternatively be distally advanced to recapture distal or second end 118 of stent 102 and/or anti-paravalvular leakage component 730. If recapture is desired, distal advancement of sheath 846 causes anti-paravalvular leakage component 730 to unroll and approach its substantially linear compressed configuration discussed herein with respect to FIGS. 8A and 8B.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A transcatheter valve prosthesis comprising:
   a tubular stent having a compressed configuration for delivery within a vasculature and an expanded configuration for deployment within a native heart valve;
   a prosthetic valve component disposed within and secured to the stent; and
   a plurality of self-expanding struts, each strut having a first end coupled to a distal end of the tubular stent and a free end not coupled to the tubular stent, wherein each strut is moveable between a compressed configuration in which the strut extends distally away from the distal end of the stent and a deployed configuration in which the strut has a C-shape that extends proximally away from the distal end of the stent and is twisted such that the C-shape is oriented substantially flush with an outer surface of the stent.

2. The transcatheter valve prosthesis of claim 1, wherein each strut has a partially deployed configuration when transforming between the compressed configuration and the deployed configuration in which the strut has a C-shape that extends radially away from the outer surface of the tubular stent.

3. The transcatheter valve prosthesis of claim 2, wherein the strut is oriented within a plane taken through a longitudinal axis of the tubular stent when in the partially deployed configuration.

4. The transcatheter valve prosthesis of claim 1, wherein each strut has a partially deployed configuration when transforming between the compressed configuration and the deployed configuration in which the strut has a C-shape that extends circumferentially around at least a portion of the tubular stent.

5. The transcatheter valve prosthesis of claim 1, wherein each strut extends generally parallel with a longitudinal axis of the tubular stent when in the compressed configuration.

6. The transcatheter valve prosthesis of claim 1, further comprising:
   a sealing membrane coupled to the plurality of self-expanding struts such that the membrane encircles the outer surface of the tubular stent when in the deployed configuration.

7. The transcatheter valve prosthesis of claim 6, wherein a diameter of the sealing membrane is greater than an expanded outer diameter of the tubular stent such that sealing material of the membrane between the struts billows.

8. The transcatheter valve prosthesis of claim 6, wherein the sealing membrane includes a first layer coupled to an inner surface of the struts and a second layer coupled to an outer surface of the struts, thereby sandwiching the struts between the first and the second layer of sealing membrane.

9. The transcatheter valve prosthesis of claim 1, wherein the struts are spaced apart in approximately equal intervals around the tubular stent.

10. A transcatheter valve prosthesis comprising:
    a tubular stent having a compressed configuration for delivery within a vasculature and an expanded configuration for deployment within a native heart valve;
    a prosthetic valve component disposed within and secured to the stent; and
    an anti-paravalvular leakage component coupled to and encircling an outer surface of the tubular stent, the anti-paravalvular leakage component including a plurality of self-expanding struts and an annular sealing membrane coupled to the struts, each strut having a first end coupled to a distal end of the tubular stent and a free end not coupled to the tubular stent, wherein the anti-paravalvular leakage component is moveable between a compressed configuration in which each strut extends distally away from the distal end of the stent and a deployed configuration in which each strut has a C-shape that extends proximally away from the distal end of the stent and is twisted such that the C-shape lies in a plane tangential with an outer surface of the stent or a plane parallel to the plane tangential with the outer surface of the stent.

11. The transcatheter valve prosthesis of claim 10, wherein the anti-paravalvular leakage component has a partially deployed configuration when transforming between the compressed configuration and the deployed configuration in which each strut has a C-shape that extends radially away from the outer surface of the tubular stent and is oriented within a plane taken through a longitudinal axis of the tubular stent.

12. The transcatheter valve prosthesis of claim 10, wherein the anti-paravalvular leakage component has a partially deployed configuration when transforming between the compressed configuration and the deployed configuration in which the strut has a C-shape that extends circumferentially around at least a portion of the tubular stent.

13. The transcatheter valve prosthesis of claim 10, wherein each strut extends generally parallel with a longitudinal axis of the tubular stent when the anti-paravalvular leakage component is in the compressed configuration.

14. The transcatheter valve prosthesis of claim 10, wherein a diameter of the sealing membrane is greater than an expanded outer diameter of the tubular stent such that sealing material of the membrane between the struts billows.

15. The transcatheter valve prosthesis of claim 10, wherein the sealing membrane includes a first layer coupled to an inner surface of the struts and a second layer coupled to an outer surface of the struts, thereby sandwiching the struts between the first and the second layer of sealing membrane.

* * * * *